(12) United States Patent
Mandava et al.

(10) Patent No.: US 10,877,013 B2
(45) Date of Patent: Dec. 29, 2020

(54) SYSTEM, METHOD, AND APPARATUS FOR CONDITION MONITORING OF FOOD AND OTHER PERISHABLE PRODUCTS AS WELL AS ENVIRONMENTALLY SENSITIVE INDUSTRIAL SUPPLY CHAINS

(71) Applicant: Inteligistics, Inc., Pittsburgh, PA (US)

(72) Inventors: Panduranga Rao Mandava, Pittsburgh, PA (US); Erick John Muriungi Kithinji, Pittsburgh, PA (US)

(73) Assignee: Inteligistics, Inc., Pittsburgh, PA (US)

( * ) Notice: Subject to any disclaimer, the term of this patent is extended or adjusted under 35 U.S.C. 154(b) by 258 days.

(21) Appl. No.: 15/720,675

(22) Filed: Sep. 29, 2017

(65) Prior Publication Data

US 2018/0088098 A1 Mar. 29, 2018

Related U.S. Application Data

(60) Provisional application No. 62/401,395, filed on Sep. 29, 2016.

(51) Int. Cl.
*G01N 33/02* (2006.01)
*G06Q 10/08* (2012.01)
*G01K 1/02* (2006.01)

(52) U.S. Cl.
CPC ............. *G01N 33/02* (2013.01); *G01K 1/022* (2013.01); *G01K 1/024* (2013.01); *G01K 1/026* (2013.01); *G06Q 10/0832* (2013.01); *G06Q 10/0833* (2013.01); *G01K 2207/04* (2013.01)

(58) Field of Classification Search
None
See application file for complete search history.

(56) References Cited

U.S. PATENT DOCUMENTS

| | | | |
|---|---|---|---|
| 2009/0303052 A1* | 12/2009 | Aklepi .................. | G06Q 10/08 340/573.2 |
| 2011/0029413 A1* | 2/2011 | Ben-Tzur ............... | G06Q 10/08 705/28 |
| 2012/0039356 A1* | 2/2012 | Adams ..................... | G01K 7/00 374/155 |
| 2013/0185675 A1* | 7/2013 | Perry .................... | G06F 3/0481 715/832 |

(Continued)

*Primary Examiner* — Gregory J Toatley, Jr.
*Assistant Examiner* — Terence E Stifter, Jr.
(74) *Attorney, Agent, or Firm* — The Webb Law Firm

(57) ABSTRACT

The present invention relates to a system, method, and apparatus for monitoring food products. The system includes an integrated modular sensing device for monitoring food and environmentally sensitive industrial products, including a processor, at least two interfaces in communication with the processor and adapted to receive an electronic connection of at least two temperature sensor probes, at least one sensor in communication with the processor, the at least one sensor including at least one of the following: a motion sensor, a proximity sensor, a light sensor, or any combination thereof, and a wireless communication device programmed or configured to transmit food and environmentally sensitive industrial product data to at least one of a remote server and a remote device, and act as a gateway to receive sensory data from distributed sensors wirelessly and upload to cloud databases.

20 Claims, 6 Drawing Sheets

(56) References Cited

U.S. PATENT DOCUMENTS

2015/0300887 A1* 10/2015 Mandava ............... G01K 1/024
  702/130
2016/0260059 A1*  9/2016 Benjamin .......... G06Q 10/0832
2016/0341709 A1* 11/2016 Huang .................... H04W 4/70

* cited by examiner

SYSTEM, METHOD, AND APPARATUS FOR CONDITION MONITORING OF FOOD AND OTHER PERISHABLE PRODUCTS AS WELL AS ENVIRONMENTALLY SENSITIVE INDUSTRIAL SUPPLY CHAINS

CROSS REFERENCE TO RELATED APPLICATIONS

This application claims the benefit of U.S. Provisional Patent Application No. 62/401,395, filed on Sep. 29, 2016, the disclosure of which is hereby incorporated by reference in its entirety.

BACKGROUND OF THE INVENTION

Field of the Invention

This invention relates generally to monitoring food and perishable products such as flowers, pharmaceuticals, healthcare products and environmentally sensitive industrial products and, in particular, to a system, method, and apparatus for monitoring various parameters and environmental conditions of food and perishable products during harvesting, processing, transportation, storage, and point-of-sale, as well as environmentally sensitive industrial products. Food products generally means all perishable and temperature sensitive products whose quality and shelf life is dependent on maintaining them in certain temperature range(s) for safekeeping. Environmentally sensitive industrial products generally means all industrial products whose life cycles and operational requirements are dependent on maintaining them in certain ranges of temperature, humidity, vibration, light, salinity and insecticide range(s) for safekeeping. The environmentally sensitive industrial products include a cross section of automotive, industrial and medical and chemical machines used in manufacturing products that require them to be maintained in an appropriate conditions for ensuring the end products meet certain hygenic and life cycle preservation. From here onwards, reference to food products and their safekeeping by environmental protecting will also include the protection and safekeeping of environmentally sensitive industrial products.

Description of Related Art

Typically, the temperature of food products, such as the pulp-temperature of fresh produce or food stored for retail sales, is measured with a temperature sensor that is manually inserted into a food product packaged in pallets, bins, totes or boxes during harvesting, pre-cooling, cold storage warehouses, processing, transportation, or while on retail store shelves. Such methods require labor to regularly check the temperatures to determine when a food product must be cooled or heated to bring temperatures to an acceptable level or moved to a location having an acceptable temperature. When fresh produce is harvested, it should be quickly cooled to a low temperature (e.g., 32° F. for certain fruits and vegetables) in order to enhance quality and extend shelf life and freshness. Manual temperature probing under these circumstances is especially inefficient and problematic. A manual approach results in decreased throughput of food products and increased costs and potentially lower quality and depleted shelf life and freshness. Likewise, humidity of the environment of the enclosure where the food resides has certain effects on certain food products. In a similar way certain environmentally sensitive industrial products are required to be maintained under certain ranges of environmental conditions that were mentioned in the previous paragraph in an automated fashion in order to improve safety and efficiency and avoid increased costs and potentially lower quality and depleted life cycles.

Moreover, simply keeping track of the temperature of food products does not provide sufficient information about the care, handling, and/or environmental exposure the food products were subjected to during harvesting, processing, transportation, storage, and/or point-of-sale. In order to obtain more parameters and for collecting and compiling data concerning the food products, multiple devices and components would have to be utilized. This would lead to a high cost of integration and an end product that is bulky in size and shape, and also requires multiple software solutions for obtaining the information and updating the devices, as an example.

SUMMARY OF THE INVENTION

Accordingly, and generally, provided are improved systems, methods, and apparatuses for monitoring food and other perishable products and environmentally sensitive industrial products that address or overcome certain drawbacks and deficiencies in existing systems and processes.

According to a preferred and non-limiting embodiment of the present invention, provided is an integrated modular sensing device for monitoring food products, including: a processor; at least two interfaces in communication with the processor and adapted to receive an electronic connection of at least two temperature sensor probes to collect the true product temperature; at least one sensor in communication with the processor, the at least one sensor comprising at least one of the following: a motion sensor, a proximity sensor, a light sensor, a gas sensor, or any combination thereof; and a wireless communication device programmed or configured to transmit food product data to at least one of a remote server and a remote device.

In non-limiting embodiments, the processor may be programmed or configured to generate the food product data based on sensor data received from the at least two temperature sensor probes and the at least one sensor. Moreover, the at least one sensor may include at least two of the following: an accelerometer, a gyroscope, a magnetometer, a force sensor, a vibration sensor, a humidity sensor, an ambient light sensor, a proximity sensor, an ambient temperature sensor, an infra-red temperature sensor, a gas sensor, a pressure sensor, or any combination thereof. In some examples, the wireless communication device may include at least one of the following: a cellular communication device, a wireless network communication device or interface, a Bluetooth communication device, a ZigBee communication device, a Narrowband IoT (NB-IoT) communication device, a Satellite communication device, or any combination thereof. The integrated modular sensing device may also include an analog front-end in communication with the at least two interfaces and the processor, and/or a global positioning satellite (GPS) receiver in communication with the processor, wherein the processor is programmed or configured to determine a location of the integrated modular sensing device based at least partially on location data received by the GPS receiver.

According to another preferred and non-limiting embodiment of the present invention, provided is a method for monitoring food products, including: receiving, from a plurality of temperature sensor probes from a first integrated modular sensing device, temperature data over a wireless network, wherein the plurality of temperature sensors are adapted for insertion into a food product, and wherein the temperature data comprises a pulp-temperature of the food product; generating food product data from the temperature data and sensor data obtained from at least one other sensor arranged in the first integrated modular sensing device, the at least one other sensor comprising at least one of the following: a motion sensor, a proximity sensor, a light sensor, or any combination thereof; storing the food product data in at least one data structure; and generating data configured to display, on at least one user computer, a graphical user interface based at least partially on the food product data.

Non-limiting embodiments of the invention further may be characterized by one or more of the following clauses:

Clause 1: An integrated modular sensing device for monitoring food products, comprising: a processor; at least two interfaces in communication with the processor and adapted to receive an electronic connection of at least two temperature sensor probes; at least one sensor in communication with the processor, the at least one sensor comprising at least one of the following: a motion sensor, a proximity sensor, a light sensor, or any combination thereof; and a wireless communication device programmed or configured to transmit food product data to at least one of a remote server and a mobile device.

Clause 2: The integrated modular sensing device of Clause 1, wherein the processor is programmed or configured to generate the food product data based on sensor data received from the at least two temperature sensor probes and the at least one sensor.

Clause 3: The integrated modular sensing device of Clause 1 or 2, wherein the at least one sensor comprises at least one of the following: an accelerometer, a gyroscope, a force sensor, a vibration sensor, a humidity sensor, an ambient light sensor, the proximity sensor, an ambient temperature sensor, a gas sensor, a pressure sensor, or any combination thereof.

Clause 4: The integrated modular sensing device of any of the preceding clauses, wherein the wireless communication device comprises at least one of the following: a cellular communication device, a wireless network communication device or interface, a Bluetooth communication device, a ZigBee communication device, a Narrowband IoT (NB-IoT) communication device, a Satellite communication device, an Ethernet communication device, or any combination thereof.

Clause 5: The integrated modular sensing device of any of the preceding clauses, further comprising an analog front-end in communication with the at least two interfaces and the processor.

Clause 6: The integrated modular sensing device of any of the preceding clauses, further comprising a global positioning satellite (GPS) receiver in communication with the processor, wherein the processor is programmed or configured to determine a location of the integrated modular sensing device based at least partially on location data received by the GPS receiver.

Clause 7: The integrated modular sensing device of any of the preceding clauses, wherein the processor is programmed or configured to determine a location of the integrated modular sensing device based at least partially on GPS signals, wireless network signals, cellular tower signals, or any combination thereof.

Clause 8: The integrated modular sensing device of any of the preceding clauses, wherein the processor is programmed or configured to: monitor sensor data from the at least two temperature sensor probes and/or the at least one sensor; determine if the sensor data meets or exceeds at least one predetermined threshold value; and in response to determining that the sensor data meets or exceeds the at least one predetermined threshold value, generating at least one alert.

Clause 9: The integrated modular sensing device of any of the preceding clauses, wherein the processor is further programmed or configured to transmit the at least one alert to at least one individual via at least one of the following: email; text message; telephone voice call; web-based message; or any combination thereof.

Clause 10: The integrated modular sensing device of any of the preceding clauses, wherein the external sensors further comprise one of a pressure sensor, a gas sensor, or any combination thereof.

Clause 11: The integrated modular sensing device of any of the preceding clauses, wherein the integrated modular sensing device receives data from one or more distributed sensors, processes the data, and transmits the data to a remote database for further processing and transmission to a user.

Clause 12: A computer-implemented method for monitoring food products, comprising: receiving, from a plurality of temperature sensor probes from a first integrated modular sensing device, temperature data over a wireless network, wherein the plurality of temperature sensors are adapted for insertion into a food product, and wherein the temperature data comprises a pulp-temperature of the food product; generating food product data from the temperature data and sensor data obtained from at least one other sensor arranged in the first integrated modular sensing device, the at least one other sensor comprising at least one of the following: a motion sensor, a proximity sensor, a light sensor, or any combination thereof; storing the food product data in at least one data structure; and generating data configured to display, on at least one user computer or a mobile device, a graphical user interface based at least partially on the food product data.

Clause 13: The computer-implemented method for monitoring food products of Clause 12, wherein the wireless network comprises a cellular communication device, Bluetooth communication device, a ZigBee communication device, a Narrowband IoT (NB-IoT) communication device, a Satellite communication device, an Ethernet communication device, or any combination thereof.

Clause 14: The computer-implemented method for monitoring food products of any of clauses 12-13, further including: obtaining location data of the first integrated modular sensing device; storing the location data in at least one data structure; and displaying the location data on the graphical user interface.

Clause 15: The computer-implemented method for monitoring food products of any of clauses 12-14, wherein the location data is obtained based at least partially on GPS signals, wireless network signals, cellular tower signals, or any combination thereof.

Clause 16: The computer-implemented method for monitoring food products of any of clauses 12-15, further comprising: monitoring the food product data; determining if the food product data meets or exceeds at least one predetermined threshold value; and generating at least one alert if the food product data meets or exceeds the at least one predetermined threshold value.

Clause 17: The computer-implemented method for monitoring food products of any of clauses 12-16, further comprising: transmitting the at least one alert to at least one individual via at least one of the following: email, text message, telephone voice call, web-based message, or any combination thereof.

Clause 18: A computer program product for monitoring food products, comprising at least one non-transitory computer-readable medium including program instructions that, when executed by at least one processor, cause the at least one processor to: receive, from a plurality of temperature sensor probes from a first integrated modular sensing device, temperature data over a wireless network, wherein the plurality of temperature sensors are adapted for insertion into a food product, and wherein the temperature data comprises a pulp-temperature of the food product; generate food product data from the temperature data and sensor data obtained from at least one other sensor arranged in the first integrated modular sensing device, the at least one other sensor comprising at least one of the following: a motion sensor, a proximity sensor, a light sensor, or any combination thereof; store the food product data in at least one data structure; and generate data configured to display, on at least one user computer or a mobile device, a graphical user interface based at least partially on the food product data.

Clause 19: The integrated modular sensing device of any of the preceding clauses further performs as a gateway to collect the environmental data provided a number of distributed sensor devices located in its vicinity using Bluetooth, Zigbee, Wi-fi or other wireless communication methods and process the information and upload to cloud databases for further processing and dissemination for useful monitoring of the distributed products that are represented by the distributed sensor devices.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE INVENTION

Figure 1:
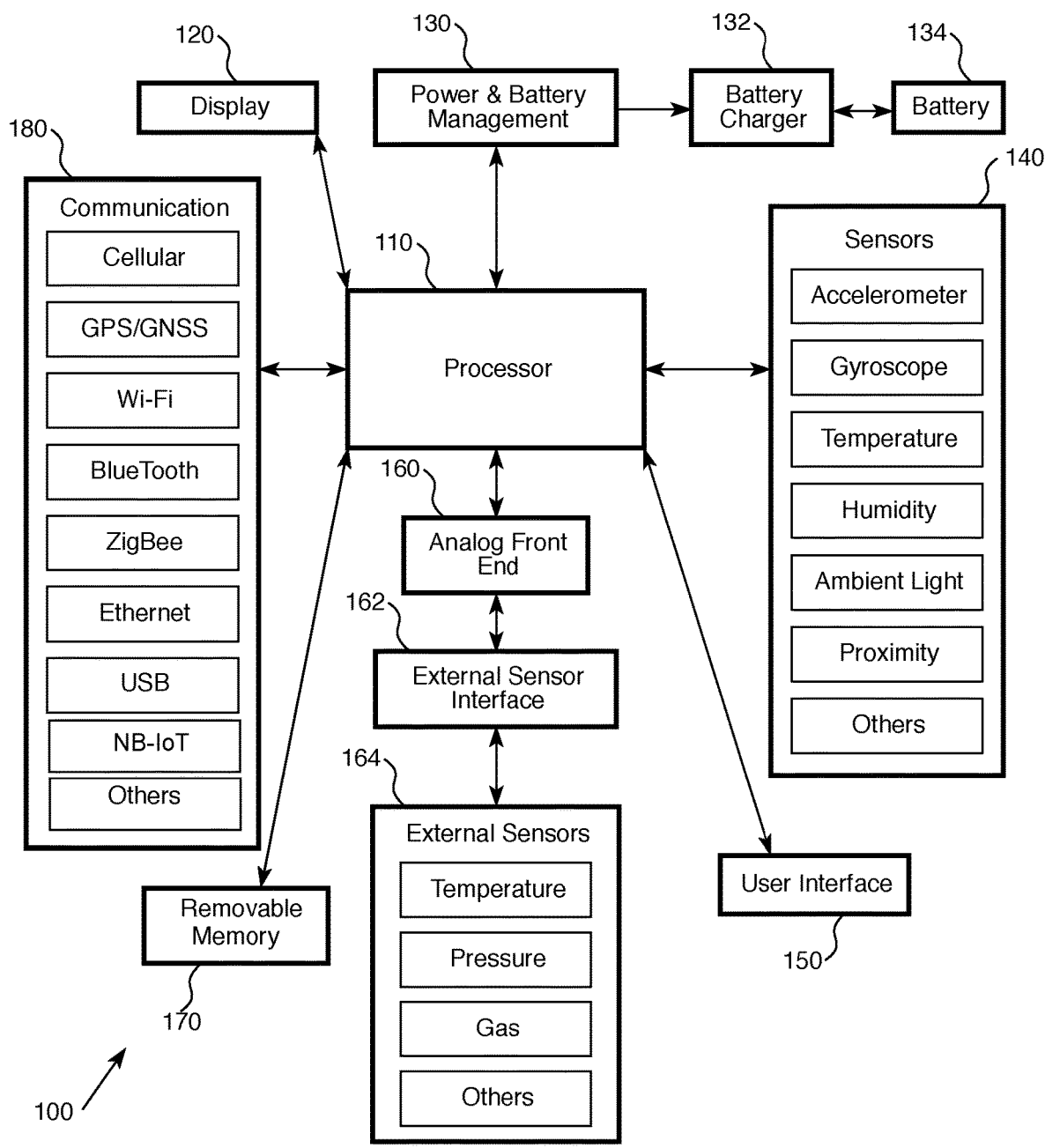
FIG. 1 depicts a schematic representation of an example of a modular sensing device and system according to a non-limiting embodiment.

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated and described in the following specification are simply exemplary embodiments of the invention. Hence, specific dimensions and other physical characteristics related to the embodiments disclosed herein are not to be considered as limiting.

As used herein, the terms "communication" and "communicate" refer to the receipt or transfer of one or more signals, messages, commands, or other types of data. For one unit or device to be in communication with another unit or device means that the one unit or device is able to receive data from and/or transmit data to the other unit or device. A communication may use a direct or indirect connection, and may be wired and/or wireless in nature. Additionally, two units or devices may be in communication with each other even though the data transmitted may be modified, processed, routed, etc., between the first and second unit or device. For example, a first unit may be in communication with a second unit even though the first unit passively receives data, and does not actively transmit data to the second unit. As another example, a first unit may be in communication with a second unit if an intermediary unit processes data from the first unit and transmits processed data to the second unit. It will be appreciated that numerous other arrangements are possible.

As used herein, the term "food product" may refer to one or more food items such as, for example, produce (e.g., fruits and vegetables), meat products (e.g., cooked meats, raw meats, etc.), and/or any other like products, such as flowers, that may be perishable and/or affected by temperature, humidity, movement, light, and/or the like as well as environmentally sensitive industrial products As used herein, the terms "cooling container" and "container" may refer to any container, room, or chamber that is used to cool food products, including those that use vacuums or fans to remove heat, and may or may not use coolants. It will be appreciated that the present invention contemplates the use of various types of cooling containers and methods, including but not limited to, forced air cooling, vacuum tube cooling, and various forms of cold storage including refrigerated transportation. Moreover, it will be appreciated that the system may also be used with other perishable items such as, for example, pharmaceutical products, biological specimens, and the like and non-perishable environmentally sensitive industrial products.

The present invention may be used in combination with features of the system, method, and apparatus for temperature monitoring and visibility disclosed in U.S. patent application Ser. No. 14/691,964 to Mandava et al., published as U.S. Patent Application Publication No. 2015/0300887, the entirety of which is hereby incorporated by reference. For example, the integrated modular sensing device described herein may be used with the system described in U.S. patent application Ser. No. 14/691,964, including the server-side components, temperature sensing device, graphical user interfaces, and/or the like.

According to a preferred and non-limiting embodiment of the present invention, a system, method, and apparatus are provided for monitoring various food products and other perishable items during processing, transportation, storage, and point-of-sale. The system can be used to monitor the conditions and handling of food products from farm to table and may include an integrated modular sensing device that incorporates several different sensors for monitoring food product data relating to the processing, transportation, storage, and sale of food products. The system provides an integrated electronics solution for advanced intelligent logistics tracking and reporting, and is designed in a modular way that allows for the inclusion/exclusion of modules through hardware population and software settings. The modular design allows for variants with additional communication methods and additional sensors.

As used herein, the term "food product data" refers to one or more parameters, records, or other types of information relating to the processing, storage, transportation, and/or point-of-sale of one or more food products. Food product data may include, for example, food product temperature, humidity, movement, light exposure, gas exposure, location, position, orientation, proximity to objects or entities, and/or any other like sensor data or values extrapolated from such sensor data. Food product data may be associated with a time and/or date or a range of times and/or dates. For example, food product data may include raw sensor data and/or sensor data that is aggregated, averaged, and/or processed in various ways.

With reference to FIG. 1, an example of an integrated modular sensing device 100 according to the present disclosure may include one or more internal sensors 140. Examples of sensors are one or more temperature sensor probes for pulp temperature measurement, ambient temperature and humidity sensors, a GPS receiver, motion sensors, vibration sensors, proximity sensors, orientation sensors, ambient light sensors, and/or other like components. The motion sensors may include, for example, accelerometers, gyroscopes, magnetometers and/or force transducers, and the proximity sensors may include infrared, laser, optical, and/or other types of sensors capable of determining that an object or entity is in proximity. It will be appreciated that various other sensors are possible.

The integrated modular sensing device 100 further includes one or more processors 110, such as, but not limited to, controllers, microprocessors, CPUs, and/or other like computing devices. The integrated modular sensing device 100 may also include various communication devices 180 capable of communicating via various networks and protocols including, for example, cellular (e.g., GSM/GPRS, UMTS/HSPA (+), CDMA and LTE cat. (1, 3, and 4), etc.), a Narrowband IoT (NB-IoT) communication device, a Satellite communication device, GPS, GNSS, Wi-Fi, Bluetooth, ZigBee, nearfield communication (NFC), infrared, Ethernet, USB, and/or other like communication networks and protocols. The system may utilize one or more communication devices to transfer data, obtained from multiple on-board and interfaced sensors, to remote servers and to retrieve firmware and setting updates, as examples. It is to be understood that the number of communication devices 180 may be greater, equal to, or less than the number of sensors discussed herein in relation to FIG. 1.

An example of integrated modular sensing device 100 includes a cellular communication mode, wherein the communication devices 180 include a cellular communications device. Cellular devices may be available in different form factors and variants to provide the flexibility for scaling different cellular technologies to various applications and geographical requirements such as bands, cost and performance and level of component integration. The integrated modular sensing device 100 may be designed with flexible cellular connectivity options for worldwide operation.

Examples of the integrated modular sensing device 100 may further include one or more electronic displays 120, cameras, RFID transponders and/or receivers, interfaces for wired and/or wireless auxiliary sensors, a rechargeable or replaceable battery 134, and/or other like components. In one non-limiting example, a single circuit board (e.g., a Printed Circuit Board (PCB)), not shown, may be used to integrate multiple temperature probes and other sensors into a single device.

With further reference to FIG. 1, a preferred and non-limiting embodiment of the integrated modular sensing device 100 includes a processor 110, an analog front-end 160, one or more communication ports and/or devices 180 in operable communication with the processor 110, removable memory 170, such as a microSD card in operable communication with the processor 110, a display 120, such as a liquid crystal display (LCD) or other display device, a power and battery management unit or circuit 130, and a power supply, such as a battery charger 132 and a battery 134, such as a lithium ion battery. The analog front-end 160 may support an external sensor interface 162 through which one or more external sensors 164 may be operably connected with the processor 110. In examples according to the present disclosure, an integrated modular sensing device 100 may include more than one external sensor interface 164. Examples of external sensors 164 may include one or more pulp temperature sensor probes, such as a thermistor, a resistance thermometer (RTD), or others known in the art. The external sensor interface 162 also may connect or communicate with pressure sensors, gas sensors (such as sensors configured to detect, carbon dioxide, oxygen, ethylene, and/or the like), and any other type of external sensor. The sensor interface 162 may be configured for wired and/or wireless connections with external sensors and devices. In examples according to the present disclosure, an integrated modular sensing device 100 may include one external sensor interface 162 that is in operable communication with two or more external sensors 164, such as temperature sensors (e.g. pulp temperature sensors). Further examples of an integrated modular sensing device 100 according to the present disclosure may include multiple external sensor interfaces 162, each of which is in operable communication with a corresponding external sensor 164, such as a temperature sensor (e.g. pulp temperature sensors). In embodiments, the analog front-end 160 may include a precision 24-bit analog-to-digital converter for temperature sensor measurement and other small signal measurements (such as ethylene gas sensors), including resistive bridge sensors.

In embodiments, the battery 134 may include a lithium-ion battery and/or lithium polymer battery, and battery charger 132 may include a highly integrated single cell lithium-ion battery charger. Power and battery management unit 130 may support operation from either a USB port or wall adapter power supply. The power and battery management unit 130 may be configured to power the integrated modular sensing device 100 from a high efficiency DC to DC converter while simultaneously and independently charging the battery. Embodiments of the power and battery management unit 130 and battery charger 132 may include a charge time optimizer with enhanced constant current (CC)/constant voltage (CV) transition, which decreases the time required for charging the battery 134; integrated field-effect transistors (FETs) for up to a 3A charge rate at 5% accuracy and 93% peak efficiency; boost capability to supply 5V at 1 A at IN for USB On-The Go (OTG) supply; an integrated power path metal-oxide-semiconductor field-effect transistor (MOSFET) and optional BGATE control to maximize battery life and instantly startup from a deeply discharged battery or no battery; a 30C input rating with over-voltage protection; and an operable temperature range from −40° C. to 85° C. Battery management functions may be programmable by a user. A power gauge also may be present on the display 120 or elsewhere on the body of the integrated modular sensing device 100 that uses current sense, coulomb counting, and accurate measurements of the battery voltage to estimate the state of charge (SOC) of the battery 134.

One or more internal sensors 140 may include, for example, an accelerometer, a gyroscope, an ambient temperature sensor, a humidity sensor, an ambient light sensor, a proximity sensor, a gas sensor, a pressure sensor, and/or the like. It is to be understood that the number of internal sensors 140 may be greater, equal to, or less than the number of sensors discussed herein in relation to FIG. 1. The integrated modular sensing device 100 may also be programmed or configured to generate a graphical user interface (GUI) 150 through the display 120 or through an external computing device, not shown, in communication with the integrated modular sensing device 100.

In an embodiment, the internal sensors 140 may include a 9-axis motion tracking device that combines a 3-axis gyroscope, a 3-axis accelerometer, a 3-axis magnetometer and a digital motion processor. The tracking device may include a 3-axis gyroscope, a 3-axis accelerometer and a 3-axis magnetometer. The accelerometer may be configured to measure orientation or tilt, velocity, and vibration/shock/impact experienced by the integrated modular sensing device 100. The 9-axis motion tracking device may trigger a motion interrupt, and may have programmable thresholds. If one of the thresholds is exceeded, an alarm state may be returned, and displayed on a display 120 and/or GUI 150.

The modular configuration of integrated modular sensing device 100 allows for the inclusion/exclusion of modules through hardware population and software settings. The modular configuration according to FIG. 1 allows for multiple internal sensors 140 and external sensors 164 to be included in or interfaced with the integrated modular sensing device 100, and for the configuration to be optimized depending on the specific needs of the user.

According to examples, one of the one or more processors 110 may be a main processor, and may include a high performance 32-bit reduced instruction set computer (RISC) processor; a digital signal processor (DSP) instruction support and floating point unit; a memory protection unit; a flexible energy management system; general purpose I/O pins; a wake up interrupt controller; direct memory access (DMA) controller; timers and/or counters; Real Time Counter (RTC); backup power domain; communication interfaces (UART, USART, SPI, I2C, USB); and have an operational temperature range spanning from −40° C. to 85° C.

In an example, software on the processor 110 may be configured to operate a power and battery management unit 130 to optimize power consumption as needed. Power consumption may be optimized by turning off unused sensors and communication devices, or disabling clocks associated with unused sensors or communication devices.

Figure 2:
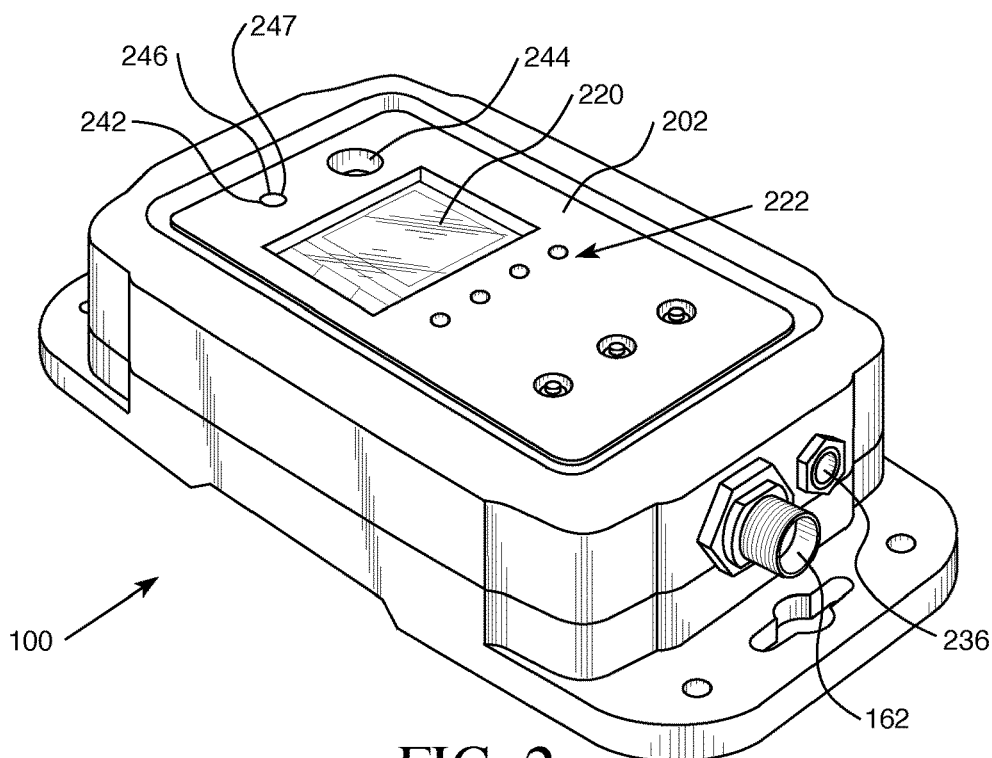
FIG. 2 depicts a perspective view of a modular sensing device according to a non-limiting embodiment.

FIG. 2 depicts a non-limiting example of an integrated modular sensing device 100 according to the present disclosure. According to the example depicted in FIG. 2, a proximity sensor 242 may be used to determine the presence of objects or entities. As shown in FIG. 2, the proximity sensor 242 may be internal to the integrated modular sensing device 100. However, external proximity sensors connected to the integrated modular sensing device 100 through, for example, the external sensor interface 162 may be used. Food product proximity data may be used, for example, to determine if food products have been neglected for a duration of time, if food products are in a high-traffic area in retail locations (for example, at point-of-sale), and/or the like. By obtaining food product data and personnel activity from a proximity sensor 242 during point-of-sale, one or more algorithms may be used to determine consumer behavior relating to the food products. For example, if food products are determined to be in a low-traffic area, the system may generate an alert or recommendation to move the food products to another location. In embodiments, proximity sensor 242 may include a built-in infrared emitter and photo-pin-diode. The proximity sensor 242 may have high resolution for proximity detection, programmable LED drive currents, and 100 Hz and 120 Hz flicker noise rejection. It is preferable for the proximity sensor 242 to have close-to-human-eye sensitivity. In embodiments, various proximity modes may be programmable by the user.

An ambient light sensor 246 may be used to determine when doors of a cooling container or truck are opened, or if a package containing the food products is opened, thereby exposing the food products to light. The ambient light sensor 246 may also be used to determine if, and for what duration, food products are being exposed to UV light and other wavelengths of light that may be harmful to the food products. For example, it may be determined if food products are placed too close to a light source in a retail location, and, therefore, need to be relocated. In examples, proximity sensor 242 and ambient light sensor 246 may be internal sensors, and may obtain data through a common window 247. The window 247 may be disposed on a front face 202 of the integrated modular sensing device 100, or otherwise configured to obtain proximity and/or light data. As shown in FIG. 2, the ambient light sensor 246 may be internal to the integrated modular sensing device 100. However, external ambient light sensors connected to the integrated modular sensing device 100 through, for example, the external sensor interface 162, may be used.

With continuing reference to FIG. 2, a humidity sensor vent 244 also may be disposed on the front face 202 of the integrated modular sensing device 100, or otherwise configured to allow humidity data to be gathered by an internal humidity sensor.

As shown in FIG. 2, an LCD display 220 and/or LED indicators 222 may be disposed on the integrated modular sensing device 100 so that they may be viewed by a user. LCD display 220 and/or LED indicators 222 may indicate sensor status, communication status, power status, and/or alarms to a user, and/or display data from the sensors to a user. The LCD display 220 and or the LED indicators 222 may be configured to indicate battery voltage level, cellular network information (such as strength and/or provider), time and date, processor firmware version, network information, error states, or any additional information required by the user. Such information may be displayed temporarily, or whenever the integrated modular sensing device 100 is powered on. The LCD display 220 may be turned on and off manually by a user.

The integrated modular sensing device 100 also may be configured to allow a user to start and/or stop the device from taking data. A state wherein the integrated modular sensing device 100 is not taking data measurements may save power or battery charge.

The example of an integrated modular sensing device 100, according to FIG. 2, includes a battery charger input 236. A power source may be connected to the input 236, which is operatively connected to a battery charger 132 to allow an internal battery 134 of the integrated modular sensing device 100 to be charged. Power may be controlled by a power switch (not shown).

The GPS receiver and/or other communication devices may be used to determine the location and/or position of food products during transportation or storage. Using GPS signals, cellular tower signals, and/or wireless network signals, as examples, the system may be able to determine a location and/or position of one or more pallets or containers of food products. For example, assisted GPS (AGPS) may be used in connection with cellular signal-based location techniques to locate a shipment of food products when the GPS does not have a clear line of sight such as, for example, when the shipment is inside buildings, between concrete buildings, and/or the like. The system may also be configured to detect GPS and/or cellular jamming and provide the appropriate results. As an example, communication devices, such as the GPS and cellular devices, may require high power consumption when in active modes, such as when transmitting or receiving data. For embodiments that use battery power, this can influence the length of time the integrated modular sensing device 100 operates before the need to recharge or replace the batteries. In non-limiting embodiments, the cellular module may detect "artificial" interference (e.g., jamming) that obscures access to the radio service and report the start and stop of such condition to the processor. This enables the processor to react appropriately such as, for example, by adjusting the data transmission intervals to the server or switching off the radio transceiver of the communication device in order to reduce power consumption and monitoring the environment at constant periods.

Figure 3:
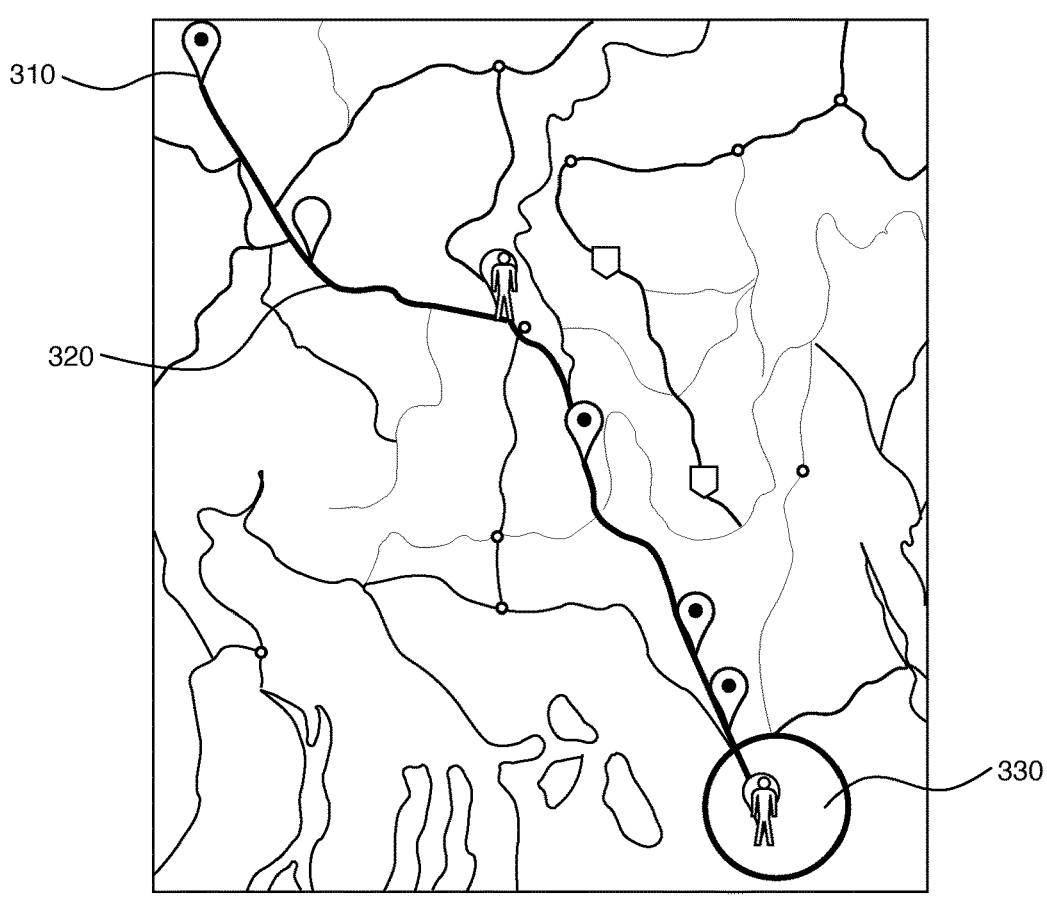
FIG. 3 depicts a schematic representation of geo-fence data obtained according to a non-limiting embodiment.

With reference to FIG. 3, a GPS receiver may be used to implement one or more geo-fences. In this manner, geographical perimeters (such as, for example, a boundary set via a radius from a central point) may be configured such that the system can determine when a particular pallet or package of food products leaves and/or arrives a designated area. The presence or lack of presence of food products from a geo-fence may trigger one or more alerts and/or a record in a database with a time stamp representing an arrival and/or departure time. In this manner, the duration of transportation and/or storage of a food product can be effectively and accurately tracked and managed. Examples of geo-fences are shown in FIG. 3, including an origination geo-fence 310, a route geo-fence 320, and a destination geo-fence 330. The origination geo-fence 310 may allow the system to determine when a shipment of food products has left its origination point. The route geo-fence 320 may be a check-in point or other in-transit geo-fence to allow the system to determine that a shipment of food products has reached a certain point along its route or to indicate that the vehicle has veered off its pre-established route. In examples, data may be gathered from one or more route geo-fences 320, and the number of route geo-fences 320 may be determined based on the distance or anticipated time of transport. The destination geo-fence 330 allows the system to determine when the shipment has reached its destination. It will be appreciated that various arrangements of geo-fences may be used.

The data that is generated and/or collected by the sensors may be used to generate one or more GUIs 150 to display the data, generate reports and/or visualizations, generate and/or display alerts, generate transportation logistics, generate point-of-sale logistics, and for other purposes.

Figure 4:
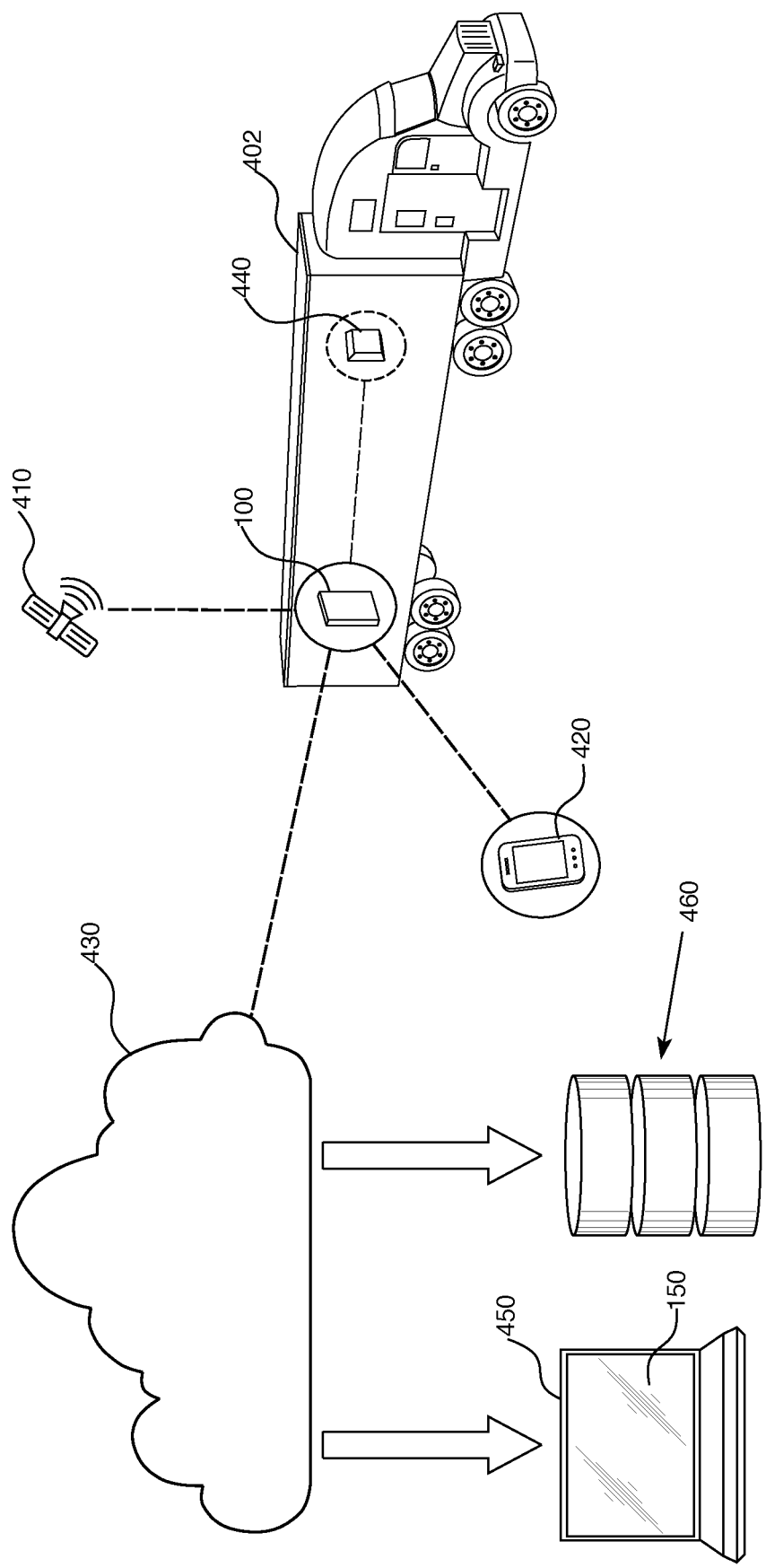
FIG. 4 depicts a schematic representation of an example of a system according to a non-limiting embodiment.

With reference to FIG. 4, the integrated modular sensing device 100 may be positioned adjacent to food products being transported in a truck 402, such that movement, location, temperature, and other properties of the food products can be sensed. The integrated modular sensing device 100 may be in communication with a satellite 410, such as a GPS satellite, a mobile device 420, additional external sensors 440, and/or a remote server 430. Communications may be through cellular, Bluetooth, Wi-Fi, ZigBee, GPS, wired, or other communication devices, as appropriate. A remote server 430 stores the collected food product data in one or more data structures 460, either remote and/or local to the server 430, and allows for the food product data to be queried by users through one or more GUIs 150.

Examples of the integrated modular sensing device 100 may include ultra-low power communication devices to provide wireless connectivity protocols such as WLAN, Bluetooth, and Zigbee. This enables different functionalities, such as interfacing with additional external sensors 440 or other integrated modular sensing devices 100 located within proximity of the ultra-low power communication device. Data may be taken over a specific environment within the range of communication of such ultra-low power communication devices—such as, for example, the trailer of a truck 402, and data on the environment may be returned to a user via, for example, a cellular connection.

The remote server 430 and/or integrated modular sensing device 100 may also monitor the food product data to generate real-time alerts in response to a trigger event such as, for example, the temperature and/or humidity being out of a desired or otherwise specified range (for example too high or too low with respect to a desired temperature range), the amount of movement exceeding predetermined thresholds, the location not matching with a planned route or destination, the presence or concentration of certain gases, and/or the like. In a preferred and non-limiting embodiment, an alert may be generated by the system (for example, a remote server 430, an integrated modular sensing device 100, a computing device 450 in communication with the server 430, or other integrated modular sensing device 100, etc.) in response to a temperature, humidity, movement, gas level, or light exposure of a food product, pallet, or storage container reaching or exceeding a specified value. Moreover, alerts may be generated in response to sensor data from an ambient light sensor 246 or other security device that indicates a security breach in an authorized location, or if the location of the food products (determined by GPS or other techniques) indicates that a vehicle transporting the food products is being routed in an unauthorized manner or if certain predetermined locations are reached. For example, entering and/or exiting a geo-fence (for example origination geo-fence 310, route geo-fence 320, or destination geo-fence 330,) may trigger a real-time alert to any stakeholder or other individual to initiate an appropriate corrective action.

The alert(s) may be displayed on a GUI 150 and/or be transmitted via email, text message, push notification, automatic telephone call, and/or the like. The method of delivery for an alert may be configured or specified by a user through a user interface 150. Further, the alerts may be customized by a user to specify a subject line, message content, recipient, or the like. For example, an email alert may specify "P101 pallet groups now ready for removal." Business rules may be defined in various ways to allow customization of such alerts and message information. As an example, software embedded in the integrated modular sensing device may compare the measured food product data with threshold values to determine if an action needs to be taken. In other examples, alerts may be generated by the server 430 by comparing the received food product data to stored thresholds.

In non-limiting embodiments, various trigger events may cause alerts to be generated or changes to be made on the GUIs 150. Threshold values and/or ranges used by the trigger events may be specified by a user or predefined. For example, different values may be used based on food products, facilities, cooling equipment, weather conditions, and/or the like. Food product data and other information received from one or more integrated modular devices 100 may also be used to determine if a trigger event has occurred. For example, a trigger event may occur if only each of multiple integrated modular sensing devices 100 detects a specified temperature or range and, in other examples, the temperatures and other values may be averaged for determining if a trigger event has occurred. Moreover, trigger events may also be based on information from multiple temperature sensor probes from a single integrated modular sensing device 100, such that the average or aggregate temperature is compared to a threshold value.

As mentioned above, the system may generate one or more graphical user interfaces (GUIs). The GUIs 150 may be generated by the integrated modular sensing device 100, the remote server 430, and/or the mobile or remote device 420 or the computer 450.

Figure 5A:
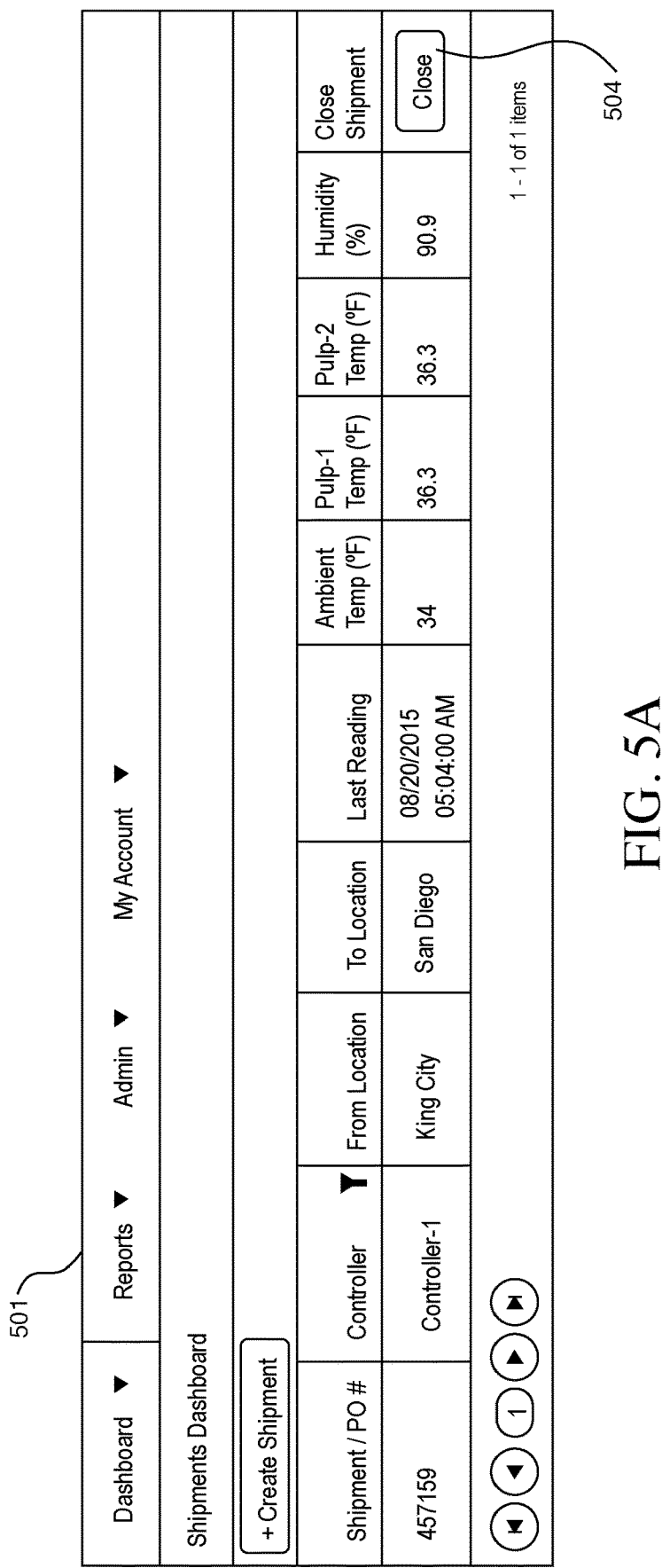
FIG. 5A depicts an example of a graphical user interface according to a non-limiting embodiment.
Figure 5B:
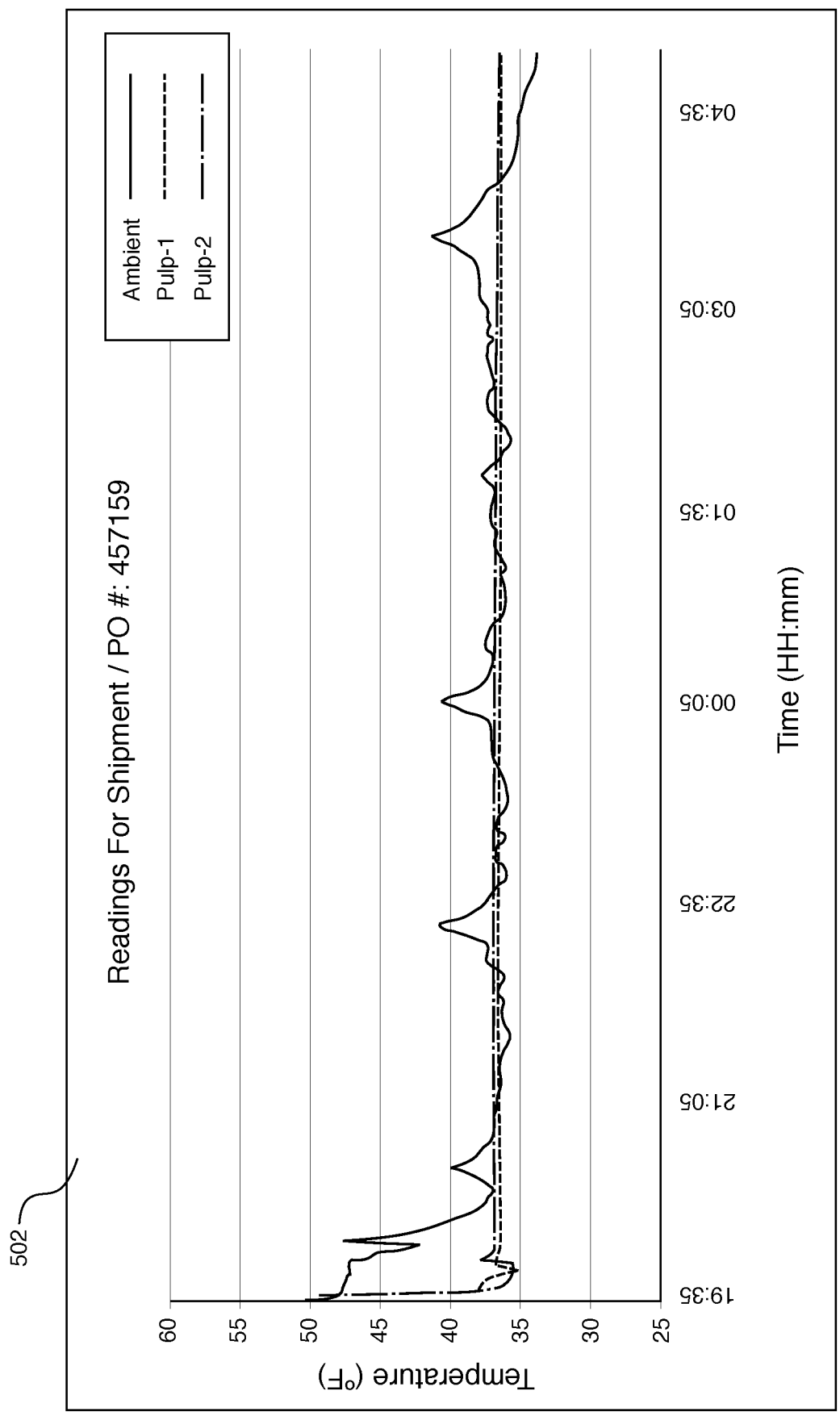
FIG. 5B depicts another example of a graphical user interface according to a non-limiting embodiment.
Figure 5C:
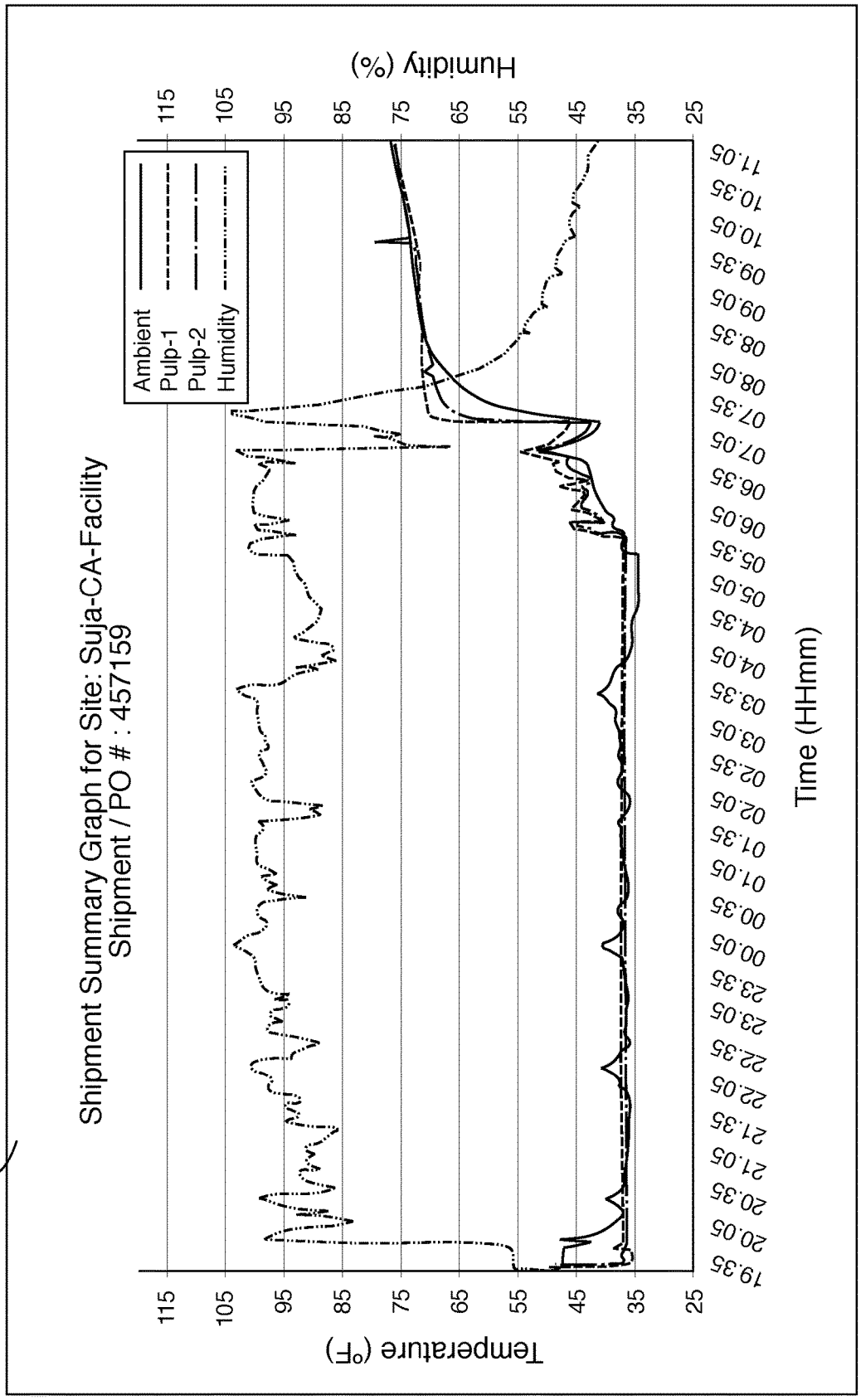
FIG. 5C depicts another example of a graphical user interface according to a non-limiting embodiment.

With reference to FIGS. 5A-5C, examples of GUIs 150 are shown according to preferred and non-limiting embodiments. GUIs 150 may show raw data taken by reports generated by the GUI 150 of FIG. 5A shows a chart 501 of shipments dashboard that identifies a shipment and/or purchase order identifier, a type of controller, a source location ("from location"), a destination location ("to location"), a time stamp from when the last measurements were taken, and food product data parameters, such as ambient temperature, a first pulp temperature (e.g., temperature data taken from a first probe of the integrated modular sensing device 100), a second pulp temperature (e.g., temperature data taken from a second probe of the integrated modular sensing device 100), and humidity (taken, for example, from a sensor connected to a humidity sensor vent 244 of the integrated modular sensing device 100). Upon selecting the shipment identifier, or another selectable option, one or more chart GUIs at FIGS. 5B-5C may be displayed. The chart 502 of FIG. 5B illustrates temperatures (ambient and pulp) over time. The chart 503 of FIG. 5C illustrates temperatures (ambient and pulp) and humidity over time. It is to be understood that the GUIs 150 of FIGS. 5A-5C may appear individually, or together as a single GUI 150. Various functionalities or reports may be generated by selecting virtual buttons, such as a virtual button 504, or drop-down menus within the GUI 150.

In a non-limiting embodiment, external sensors may communicate with the integrated modular sensing device 100. As already described, such sensors may include multiple temperature sensor probes, pressure sensors, and/or gas sensors. External sensors may also include, for example, sensors on the door of a cooling container or truck. In this manner, the integrated modular sensing device 100 may collect food product data regarding the transportation and/or storage of the food products, such as when the food products were exposed to outdoor or other environmental conditions, light, etc., and for how long. It will be appreciated that the integrated modular sensing device 100 may also communicate with various other sensors used along the supply chain including, for example, vehicle sensors in a truck transporting the food products. Communication with these sensors may be wired, or via ZigBee, BlueTooth, Wi-Fi, and the like.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An integrated modular sensing device for monitoring food products, comprising:
   a single device comprising:
      a single circuit board;
      one or more external sensor interfaces in communication with the single circuit board adapted to receive an electronic connection of at least two temperature sensor probes adapted for insertion into a single pallet or container of food product;
      a processor in communication with the single circuit board;
      at least one sensor in communication with the processor, the at least one sensor comprising at least one of the following: a motion sensor, a proximity sensor, a light sensor, an orientation sensor, or any combination thereof; and
      a wireless communication device programmed or configured to transmit food product data to at least one of a remote server and a mobile device,
   wherein the processor is programmed or configured to:
      receive information from the at least two temperature sensor probes;
      determine an average or aggregate temperature based on the information from each of the at least two temperature sensor probes inserted into the single pallet; and
      determine a trigger event based on the average or aggregate temperature.

2. The integrated modular sensing device of claim 1, wherein the processor is programmed or configured to generate the food product data based on sensor data received from the at least two temperature sensor probes and the at least one sensor.

3. The integrated modular sensing device of claim 1, wherein the at least one sensor comprises at least one of the following: an accelerometer, a gyroscope, a force sensor, a vibration sensor, a humidity sensor, an ambient light sensor, the proximity sensor, an ambient temperature sensor, a gas sensor, a pressure sensor, or any combination thereof.

4. The integrated modular sensing device of claim 1, wherein the wireless communication device comprises at least one of the following: a cellular communication device, a wireless network communication device or interface, a Bluetooth communication device, a ZigBee communication device, a Narrowband IoT (NB-IoT) communication device, a Satellite communication device, an Ethernet communication device, or any combination thereof.

5. The integrated modular sensing device of claim 1, further comprising an analog front-end in communication with the one or more external sensor interfaces and the processor.

6. The integrated modular sensing device of claim 1, further comprising a global positioning satellite (GPS) receiver in communication with the processor, wherein the processor is programmed or configured to determine a location of the integrated modular sensing device based at least partially on location data received by the GPS receiver.

7. The integrated modular sensing device of claim 1, wherein the processor is programmed or configured to determine a location of the integrated modular sensing device based at least partially on GPS signals, wireless network signals, cellular tower signals, or any combination thereof.

8. The integrated modular sensing device of claim 1, wherein the processor is programmed or configured to:
monitor sensor data from the at least two temperature sensor probes and/or the at least one sensor;
determine if the sensor data meets or exceeds at least one predetermined threshold value; and
in response to determining that the sensor data meets or exceeds the at least one predetermined threshold value, generating at least one alert.

9. The integrated modular sensing device of claim 8, wherein the processor is further programmed or configured to transmit the at least one alert to at least one individual via at least one of the following: email, text message, telephone voice call, web-based message, or any combination thereof.

10. The integrated modular sensing device of claim 1, wherein the external sensors further comprise one of a pressure sensor, a gas sensor, or any combination thereof.

11. The integrated modular sensing device of claim 1, wherein the integrated modular sensing device receives data from one or more distributed sensors, processes the data, and transmits the data to a remote database for further processing and transmission to a user.

12. The integrated modular sensing device of claim 1, wherein the at least one sensor comprises at least one proximity sensor.

13. The integrated modular sensing device of claim 12, wherein the at least one proximity sensor is configured to provide at least one of the following:
data on human traffic near the food products, data on relative position of the food products, or any combination thereof.

14. A computer-implemented method for monitoring food products, comprising:
receiving, from a plurality of temperature sensor probes from a first integrated modular sensing device, temperature data over a wireless network, wherein the plurality of temperature sensors are adapted for insertion into a single pallet or container of food product, and wherein the temperature data comprises a pulp-temperature of the single pallet or container of food product, and wherein the first integrated modular sensing device is a single device including a single circuit board arranged within the first integrated modular sensing device, the single circuit board in communication with the plurality of temperature sensor probes and at least one processor, the at least one processor arranged within the first integrated modular sensing device;
generating, with the at least one processor, food product data from the temperature data and sensor data obtained from at least one other sensor arranged in the first integrated modular sensing device, the at least one other sensor comprising at least one of the following: a motion sensor, a proximity sensor, a light sensor, or any combination thereof;
storing, with the at least one processor, the food product data in at least one data structure;
generating, with the at least one processor, data configured to display, on at least one user computer or a mobile device, a graphical user interface based at least partially on the food product data;
receiving information from the plurality of temperature sensor probes;
determining, with the at least one processor, an average or aggregate temperature based on the information from each of the plurality of sensor probes inserted into the single pallet or container; and
determining, with the at least one processor, a trigger event based on the average or aggregate temperature.

15. The computer-implemented method for monitoring food products of claim 14, wherein the wireless network comprises a Bluetooth communication device, a ZigBee communication device, a Narrowband IoT (NB-IoT) communication device, a Satellite communication device, an Ethernet communication device, or any combination thereof.

16. The computer-implemented method for monitoring food products of claim 14, further comprising:
obtaining location data of the first integrated modular sensing device;
storing the location data in at least one data structure; and
displaying the location data on the graphical user interface.

17. The computer-implemented method for monitoring food products of claim 16, wherein the location data is obtained based at least partially on GPS signals, wireless network signals, cellular tower signals, or any combination thereof.

18. The computer-implemented method for monitoring food products of claim 14, further comprising:
monitoring the food product data;
determining if the food product data meets or exceeds at least one predetermined threshold value; and
generating at least one alert if the food product data meets or exceeds the at least one predetermined threshold value.

19. The computer-implemented method for monitoring food products of claim 18, further comprising:
transmitting the at least one alert to at least one individual via at least one of the following: email, text message, telephone voice call, web-based message, or any combination thereof.

20. A computer program product for monitoring food products, comprising at least one non-transitory computer-readable medium including program instructions that, when executed by at least one processor arranged in a first integrated modular sensing device, cause the at least one processor to:
receive, from a plurality of temperature sensor probes from the first integrated modular sensing device, temperature data over a wireless network, wherein the plurality of temperature sensors are adapted for insertion into a single pallet or container of food product, wherein the temperature data comprises a pulp-temperature of the single pallet or container of food product, and wherein the first integrated modular sensing device is a single device including a single circuit board arranged within the first integrated modular sensing device, the single circuit board in communication with the plurality of temperature sensor probes and the at least one processor;

generate food product data from the temperature data and sensor data obtained from at least one other sensor arranged in the first integrated modular sensing device, the at least one other sensor comprising at least one of the following: a motion sensor, a proximity sensor, a light sensor, or any combination thereof;

store the food product data in at least one data structure;

generate data configured to display, on at least one user computer or a mobile device, a graphical user interface based at least partially on the food product data;

receive information from the plurality of temperature sensor probes;

determine an average or aggregate temperature based on the information from each of the plurality of temperature sensor probes inserted into the single pallet; and determine a trigger event based on the average or aggregate temperature.

\* \* \* \* \*